United States Patent
Saito et al.

(10) Patent No.: US 9,297,794 B2
(45) Date of Patent: Mar. 29, 2016

(54) SORPTION EXOTHERMICITY MEASUREMENT DEVICE AND SORPTION EXOTHERMICITY MEASUREMENT METHOD

(71) Applicant: Kaken Test Center, Tokyo (JP)

(72) Inventors: Toshinobu Saito, Tokyo (JP); Kanya Kuramoto, Tokyo (JP)

(73) Assignee: Kaken Test Center, Tokyo (JP)

( * ) Notice: Subject to any disclaimer, the term of this patent is extended or adjusted under 35 U.S.C. 154(b) by 82 days.

(21) Appl. No.: 14/380,547

(22) PCT Filed: Dec. 20, 2012

(86) PCT No.: PCT/JP2012/083148
§ 371 (c)(1),
(2) Date: Aug. 22, 2014

(87) PCT Pub. No.: WO2013/125145
PCT Pub. Date: Aug. 29, 2013

(65) Prior Publication Data
US 2015/0037894 A1    Feb. 5, 2015

(30) Foreign Application Priority Data
Feb. 24, 2012 (JP) .................. 2012-039260

(51) Int. Cl.
*G01N 33/36* (2006.01)
*G01N 25/48* (2006.01)

(52) U.S. Cl.
CPC ............ *G01N 33/367* (2013.01); *G01N 25/486* (2013.01)

(58) Field of Classification Search
CPC .................................................... G01N 33/36
USPC ............ 374/147–148; 422/82.12; 436/2, 147
See application file for complete search history.

(56) References Cited

U.S. PATENT DOCUMENTS

| 4,496,249 A | * | 1/1985 | Lee | ........................ G01N 30/00 374/7 |
| 5,109,716 A | * | 5/1992 | Ito | ...................... G01N 15/0893 73/38 |
| 5,342,580 A | * | 8/1994 | Brenner | ................... G01N 7/04 422/88 |
| 6,030,116 A | | 2/2000 | Yanai et al. | |

(Continued)

FOREIGN PATENT DOCUMENTS

| GB | 2230855 | * 10/1990 |
| JP | S64035476 A | 2/1989 |

(Continued)

OTHER PUBLICATIONS

Wan, Wenjie, "First Notification of Reasons for Rejection for Chinese Patent Application No. 201280065964.3," Chinese Patent Office, Sep. 28, 2015.

(Continued)

*Primary Examiner* — Arlen Soderquist
(74) *Attorney, Agent, or Firm* — Florek & Endres PLLC

(57) ABSTRACT

A sorption exothermicity measurement device (1) mainly includes: an air pump (2) that supplies dry air; a bubbling instrument (3) that humidifies dry air and supplies humidified air; a reaction measuring instrument (4) into which air flows so that the dry air or the humidified air comes in contact with a sample (10) to be measured; and a flow rate measuring instrument (5) that measures the flow rate of at least the humidified air flowing into the reaction measuring instrument (4). The reaction instruments are connected by flow paths through which the dry air or the humidified air flows. Furthermore, at least a humidified air supply system needle valve (13) that regulates the flow rate of the humidified air is included.

6 Claims, 6 Drawing Sheets

(56) References Cited

U.S. PATENT DOCUMENTS

| | | | |
|---|---|---|---|
| 6,844,198 B2* | 1/2005 | Swenson | G01N 15/088 422/68.1 |
| 7,141,210 B2* | 11/2006 | Bell | B82Y 15/00 422/50 |
| 2001/0036670 A1* | 11/2001 | Fryer | A61L 2/208 436/135 |

FOREIGN PATENT DOCUMENTS

| | | |
|---|---|---|
| JP | H01138439 A | 5/1989 |
| JP | H1018172 A | 1/1998 |
| JP | 2003337111 A | 11/2003 |
| JP | 2005097797 A | 4/2005 |
| JP | 2006329746 A | 12/2006 |
| JP | 2007171036 A | 7/2007 |

OTHER PUBLICATIONS

Yuanzhi Lei, Li Fang Xue Yuan Zhilei, "Test Method for Performance of Moisture Adsorption and Heat Releases of Textiles," China Textile Leader, China Textile Information Center (CTIC), 2011 No. 8, p. 105-106.

* cited by examiner

US 9,297,794 B2

SORPTION EXOTHERMICITY MEASUREMENT DEVICE AND SORPTION EXOTHERMICITY MEASUREMENT METHOD

TECHNICAL FIELD

The present disclosure relates to a sorption exothermicity measurement device and a sorption exothermicity measurement method, in which the sorption exothermicity of a material having the effect of heat generation due to sorption of water molecules is measured.

BACKGROUND ART

Attention has been focused on technologies to provide synthetic fibers and the like with exothermic functions due to sorption (sorption exothermic function; function of simultaneously causing absorption and adsorption to generate heat), as well known in clothing such as wool, to allow the fibers and the like in themselves to generate heat and to enhance thermal-insulation effects. The technologies have been applied not only to fibers but also to cotton-like articles, woven fabrics, knitted fabrics, non-woven fabrics, or the like. Furthermore, there have been also attempted various applications such as applications of processing the fibers, the cotton-like articles, the woven fabrics, the knitted fabrics, the non-woven fabrics, and the like with coating agents in which powdery sorption exothermic materials are dispersed, applications of dispersing the fibers, the cotton-like articles, the woven fabrics, the knitted fabrics, the non-woven fabrics, and the like in films, and applications of forming the fibers, the cotton-like articles, the woven fabrics, the knitted fabrics, the non-woven fabrics, and the like into sheet-like articles or paper. Thus, the technologies to suitably evaluate sorption exothermicity are important for promoting the development of high-value-added products.

In recent years, a method comprising, first, preconditioning a collected test piece, putting the absolutely dried test piece in a desiccator, further leaving the test piece standing to stabilize the temperature and humidity of an atmosphere in the desiccator and to also stabilize the temperature and moisture content of the test piece, thereafter carrying out release of the lid of the desiccator, or the like, to expose the test piece to a high-humidity atmosphere, and measuring the surface temperature of the test piece with a temperature sensor has been mainstream as a technology well known as a method of testing sorption exothermicity.

For example, Patent Literature 1 describes an apparatus and a method which measure an exothermic material by adsorption heat and thermal conductivity. Specifically, there has been disclosed an apparatus for measuring sorption exothermicity comprising a precise and prompt thermophysical property measurer, a measurer that measures temperature and the like, a water supplier comprising a pump and the like, and an air supplier, wherein both of temperature increased due to adsorption heat and apparent thermal conductivity can be measured.

Patent Literature 2 also describes a method and apparatus for testing exothermicity due to sorption. Specifically, there has been disclosed a method comprising laterally partitioning a reaction vessel into three by two test pieces to make one central compartment and two side compartments, setting the humidities of atmospheres in the three compartments at initial conditions, thereafter changing the atmosphere in the central compartment or in each of the side compartments to a test condition, simultaneously measuring the temperatures of the two test pieces or the vicinities thereof, and evaluating exothermicity due to the sorption of the test pieces.

CITATION LIST

Patent Literature

Patent Literature 1: Unexamined Japanese Patent Application Kokai Publication No. 2006-329746
Patent Literature 2: Unexamined Japanese Patent Application Kokai Publication No. 2003-337111

SUMMARY OF INVENTION

Technical Problem

In the apparatus and method for measuring a sorption exothermicity material described in Patent Literature 1 mentioned above, water vapor is directly supplied from the water supplier or air supplier comprising an air pump and the like to a measurement material. In the apparatus and method for testing exothermicity due to sorption disclosed in Patent Literature 2, air with initial condition humidity or test condition humidity is also directly supplied, to a sample, from a humidity-controlled atmosphere supplier that regulates the humidity of air.

However, even if the humidity of air which flows out from the suppliers is evened out, the amount of given moisture per unit time (hereinafter also simply referred to as a flow rate) varies when the air comes in contact with a sample for evaluating sorption exothermicity (measurement material) because of passing through a tube or a bubbling instrument from the pump and additionally, due to the passage of time, and accurate temperature measurement may not be performed. As a result, accurate sorption exothermicity may not be evaluated in the sample.

The present disclosure is proposed with respect to the above-mentioned circumstances, and an objective of the present disclosure is to provide a sorption exothermicity measurement device and a sorption exothermicity measurement method, in which accuracy and reproducibility are more improved.

Solution to Problem

In order to achieve the objective, a sorption exothermicity measurement device according to a first aspect of the present disclosure includes:
a dry air supplier;
a humidified air supplier;
at least one reaction measurer into which dry air supplied from the dry air supplier or humidified air supplied from the humidified air supplier flows to allow the supplied dry air or the supplied humidified air to come in contact with a held sample;
a flow rate regulator that regulates a flow rate of at least the humidified air of the dry air or the humidified air flowing into the at least one reaction measurer; and
a flow rate measurer that measures the flow rate of at least the humidified air of the dry air or the humidified air flowing into the at least one reaction measurer.

In order to achieve the objective, a sorption exothermicity measurement method according to a second aspect of the present disclosure includes:
a drying step of allowing dry air to flow into a reaction measurer in which a sample is held;

a humidification step of allowing humidified air to flow into the reaction measurer in which the sample is held, after the drying step;

a measurement step of measuring a flow rate of the humidified air flowing into the reaction measurer in the humidification step;

a regulation step of regulating the flow rate of the humidified air flowing into the reaction measurer, measured in the measurement step, to a determined flow rate; and a temperature measurement step of measuring temperature by a temperature sensor placed near the sample held in the reaction measurer in a state in which the flow rate of the humidified air is regulated in the regulation step.

Advantageous Effects of Invention

According to the present disclosure, there is provided a sorption exothermicity measurement device and a sorption exothermicity measurement method, in which accuracy and reproducibility are more improved.

DESCRIPTION OF EMBODIMENTS (Embodiment 1)

Figure 1:
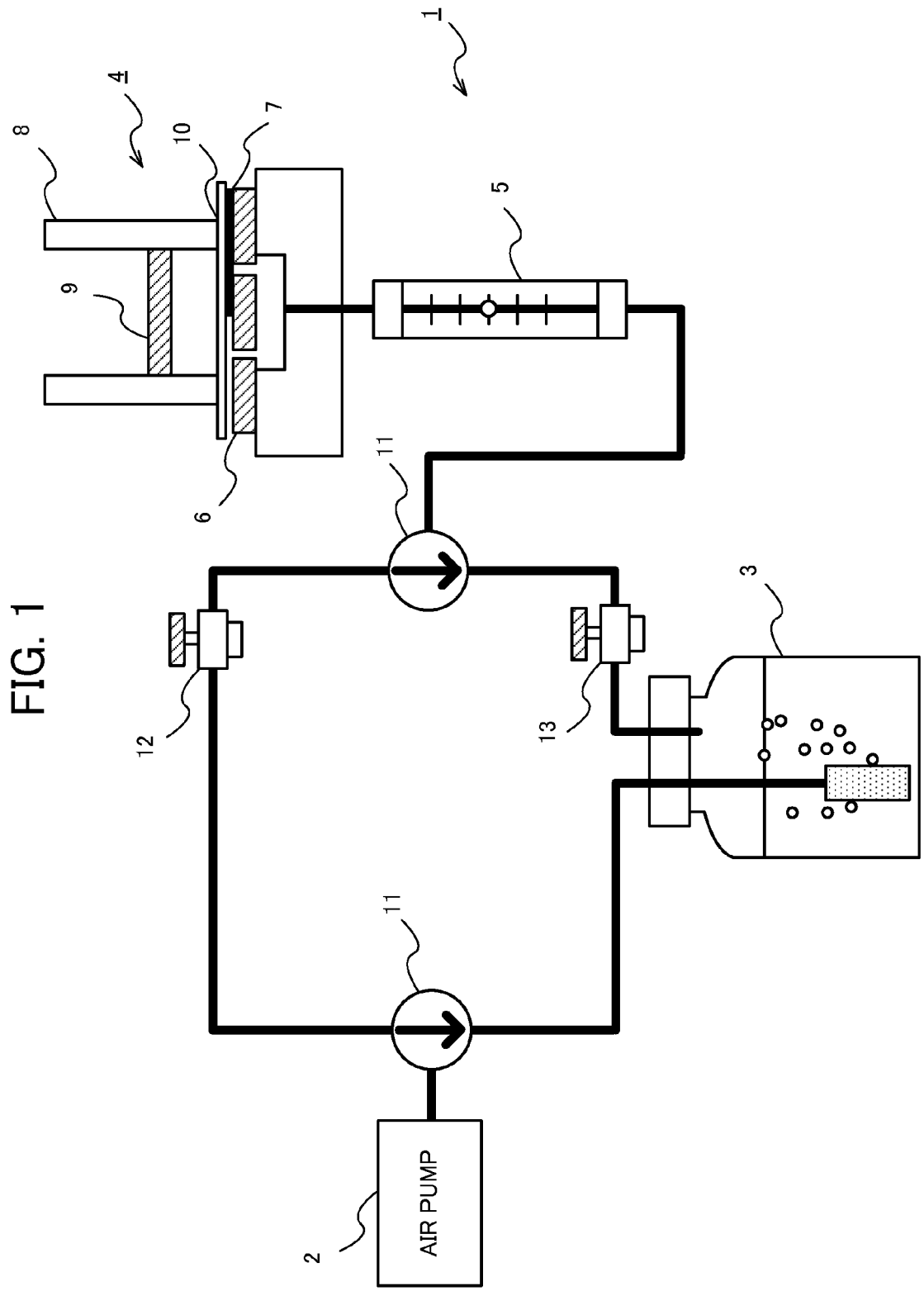
FIG. 1 is a schematic configuration diagram illustrating a sorption exothermicity measurement device according to Embodiment 1.

FIG. 1 is a schematic configuration diagram illustrating a sorption exothermicity measurement device according to Embodiment 1. As illustrated in FIG. 1, the sorption exothermicity measurement device 1 mainly includes an air pump 2, a bubbling instrument 3, a reaction measuring instrument 4, and a flow rate measuring instrument 5. The reaction instruments are connected through flow path into which dry air or humidified air flows. A switching valve 11 for switching a flow path, a dry air supply system needle valve 12 that regulates the flow rate of the dry air, and a humidified air supply system needle valve 13 that regulates the flow rate of the humidified air are disposed between the flow paths. FIG. 1 illustrates that the switching valve 11 is set in the direction of allowing air to flow through the air pump 2, the bubbling instrument 3, and the humidified air supply system needle valve 13. The reaction measuring instrument 4 includes a first foam heat-insulating material 6 on a base of the measuring instrument, a temperature sensor 7, a sample holder 8 that holds a sample 10, and a second foam heat-insulating material 9.

A method of measuring the sorption exothermicity of the sample 10 using the sorption exothermicity measurement device 1 will be explained in detail. The sample 10 means, for example, a testing piece or a molding of each of woven fabrics in which fibers are used, knits, non-woven fabrics, sheet-like articles, films, paper or powder molded articles, clothing or materials obtained by processing the fabrics, the knits, the articles, the films, the paper or the powder molded articles, or the like. Prior to the measurement, pretreatment of the sorption exothermicity measurement device 1 (supply of dry air, or the like) is preferably carried out. The temperature of the sample 10 in the case of supplying dry air is preferably measured prior to supplying humidified air.

The process of measuring the temperature of the sample 10 in the case of supplying dry air is the same as or similar to the process in the case of supplying humidified air, mentioned below, except that the switching valve 11 is set to allow the flow path to be in the direction of passing through the dry air supply system needle valve 12. Temperature just before humidified air is supplied may also be regarded as measurement temperature of dry air. In general, the flow rate of dry air need not be regulated, the dry air supply system needle valve 12 is not always needed, and the flow rate may be set at a certain flow rate. However, the flow rate of dry air may be regulated using the dry air supply system needle valve 12 in the same or similar manner as in the case of humidified air, mentioned below.

The process of measuring the temperature of the sample 10 in the case of supplying humidified air will be explained. The switching valve 11 is set to allow the flow path to be in the direction of passing through the bubbling instrument 3 containing water and the humidified air supply system needle valve 13, and humidified air is allowed to flow from the air pump 2 into the flow rate measuring instrument 5. In the flow rate measuring instrument 5, the flow rate of the humidified air is measured. In the measuring method, it is confirmed whether the flow rate of the humidified air is a flow rate within a certain range or not. In the confirmation process, for example, an operator may perform the confirmation directly by visual observation, or warning information may be sent from the flow rate measuring instrument 5 to the operator by means such as sound or light when the flow rate deviates from the certain range.

The flow rate within a certain range (also referred to as a determined value) is a flow rate within a range where a reference temperature measurement value is obtained when the sorption exothermicity of a reference standard cloth (reference cloth for evaluation, of which the sorption exothermicity has been already measured) is measured in advance. When the confirmed flow rate of humidified air deviates from the certain range, the humidified air supply system needle valve 13 is loosened or closed, for example, by manual operation, to regulate the flow rate of the humidified air to be a flow rate within the certain range. Humidified air regulated to have a flow rate within the certain range in such a manner or humidified air of which the flow rate is within the certain range when being measured passes through the base of the reaction measuring instrument 4 and flows thereinto.

Figure 2:
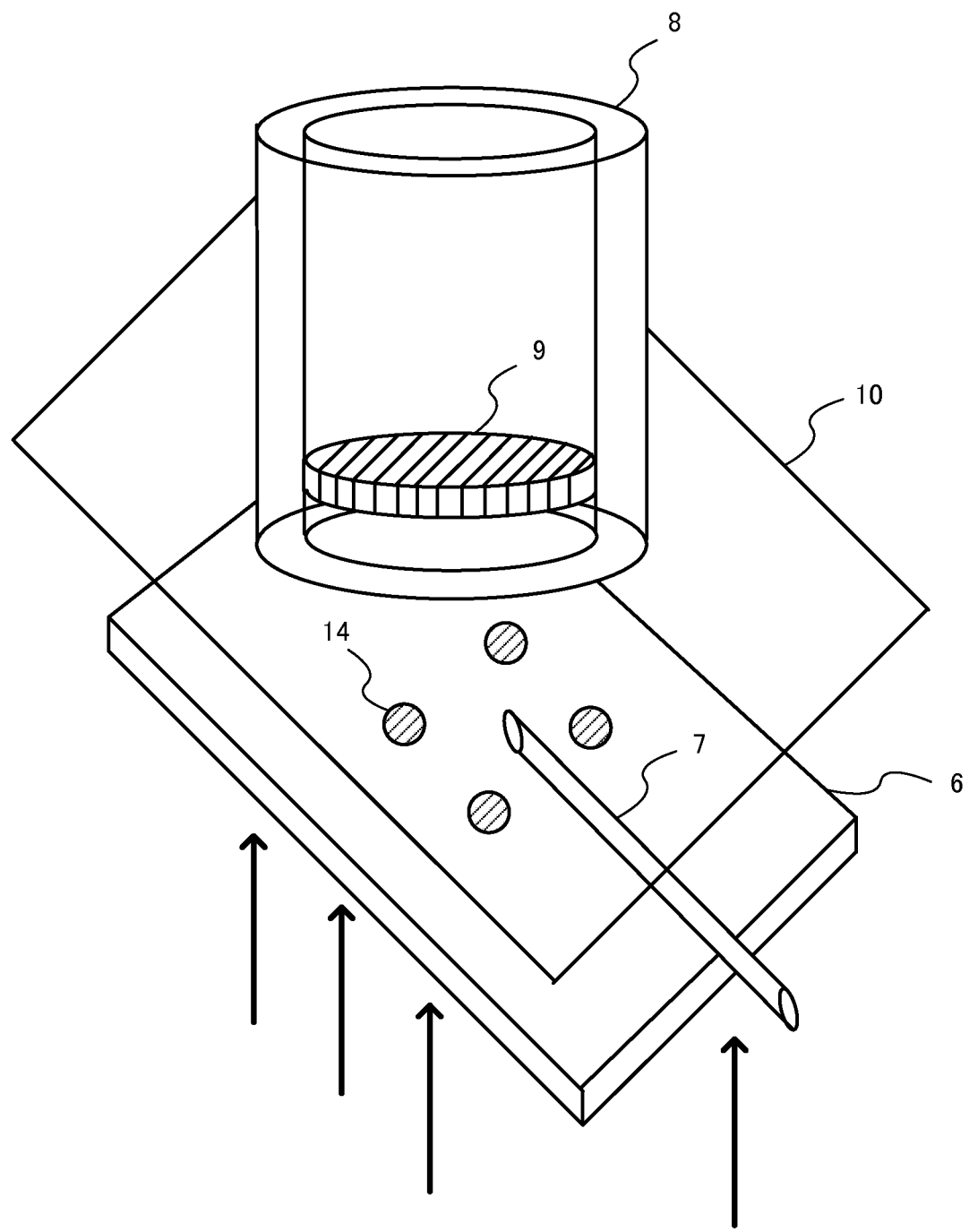
FIG. 2 is a diagrammatic perspective view illustrating the internal configuration of a reaction measuring instrument according to Embodiment 1.

FIG. 2 is a diagrammatic perspective view illustrating the internal configuration of a reaction measuring instrument according to Embodiment 1. As illustrated in FIG. 2, first, humidified air flowed into the inside of the reaction measuring instrument 4 comes in contact with the first foam heat-insulating material 6 in which discharge holes 14 are formed. The first foam heat-insulating material 6 corresponds to simulated skin in measurement of the sorption exothermicity of the sample 10. Then, inflow of the humidified air occurs from the discharge holes 14 and outflow thereof occurs toward the reverse face of the contact face of the first foam heat-insulating material 6. Although the number of the discharge holes 14 illustrated in FIG. 2 is four, the number is not limited.

As illustrated in FIG. 2, the temperature sensor 7 is placed on the reverse face of the first foam heat-insulating material 6. The temperature sensor 7 preferably has a film-like shape, and is affixed onto the face of the first foam heat-insulating material 6 with a pressure sensitive adhesive tape and/or the like. Further, the temperature-sensing portion of the temperature sensor 7 is placed to come in contact with the sample 10.

The sample holder 8 sandwiches and hold the sample 10 between the sample holder 8 and the first foam heat-insulating material 6 so that the temperature-sensing portion of the temperature sensor 7 comes in contact with the sample 10 in the periphery of a region containing the temperature sensor 7. As illustrated in FIG. 2, for example, the sample holder 8 has a cylindrical shape, and the sample 10 adheres to the bottom thereof with a tape and/or the like. When the sample 10 is a test piece of clothing or the like, the sample 10 is preferably allowed to adhere to the bottom so that the temperature sensor 7 comes directly in contact with a side to be contact with a skin, whereby sorption exothermicity can be more precisely evaluated.

The second foam heat-insulating material 9 having a circular shape is placed in the state of being packed at a spacing from the bottom, to which the sample 10 adheres, in the cylindrical shape of the sample holder 8. In detail, the second foam heat-insulating material 9 is placed in the state of facing the first foam heat-insulating material 6.

Outflow of humidified air occurs from the discharge holes 14 in the first foam heat-insulating material 6 into the reaction measuring instrument 4 having such a structure, and the temperature of the sample 10 is measured with the temperature sensor 7 every predetermined time, for example, while supplying humidified air for around 30 minutes.

When outflow of dry air or humidified air occurs from the discharge holes 14 in the first foam heat-insulating material 6, the sample 10 is sandwiched between the first foam heat-insulating material 6 and the second foam heat-insulating material 9 facing the first foam heat-insulating material 6, as illustrated in FIG. 1, and temperature is precisely measured under conditions where heat radiation due to ventilation is not likely to occur. Therefore, an evaluation similar to that under circumstances where clothing is actually worn can be performed, for example, under circumstances where the temperature of the skin-contact side of the sample 10 which is a test piece of clothing as mentioned above is directly measured.

Finally, the sorption exothermicity of the sample 10 can be evaluated by a difference between the temperature of the sample 10 in dry air and the temperature of the sample 10 in humidified air (difference between temperatures which are average temperatures or maximum end-point temperatures in measurement, or the like). When the temperature difference varies in the same sample 10 under the same conditions, supplementary testing is preferably conducted to exclude abnormal values.

As described above, in the measuring method using sorption exothermicity measurement device 1 according to the present embodiment 1, the inflow of humidified air that directly flows into the reaction measuring instrument 4 is measured and regulated, and therefore the amount of given moisture per unit time can be controlled. As a result, the evaluation results of sorption exothermicity with more accuracy and improved reproducibility can be provided.

(Embodiment 2)

Figure 3:
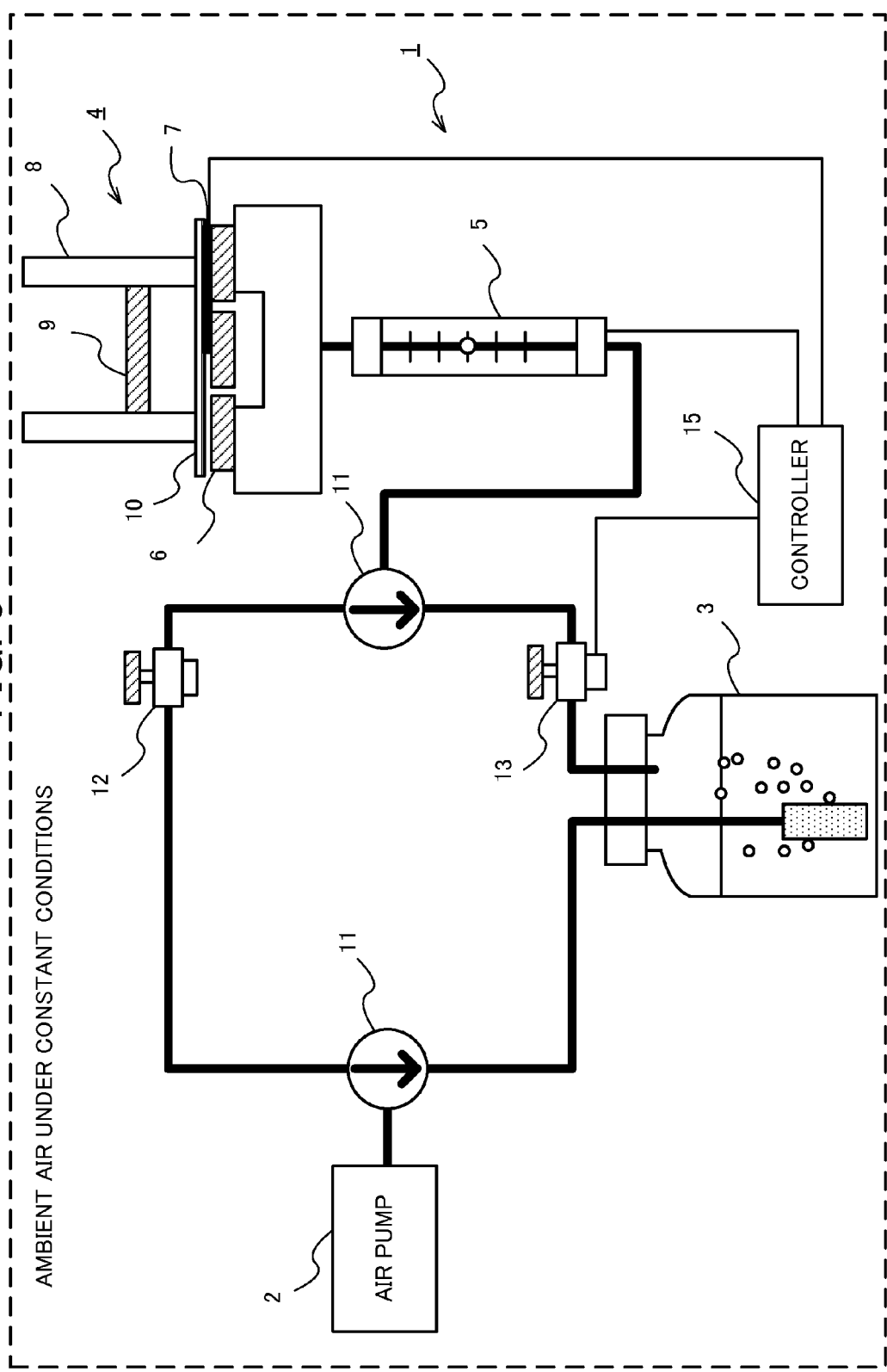
FIG. 3 is a schematic configuration diagram illustrating a sorption exothermicity measurement device according to Embodiment 2.

FIG. 3 is a schematic configuration diagram illustrating sorption exothermicity measurement device according to Embodiment 2. As illustrated in FIG. 3, the differences between the sorption exothermicity measurement device 1 according to the present embodiment 2 and the sorption exothermicity measurement device 1 according to the embodiment 1 mentioned above are in that a controller 15 is disposed between the flow rate measuring instrument 5 and the humidified air supply system needle valve 13 and in that the sorption exothermicity measurement device 1 is placed in ambient air under constant conditions.

The measurement of sorption exothermicity in ambient air under constant conditions (for example, in room with a steady temperature and humidity or the like) is preferred since the temperature of air supplied from the air pump 2 is constant and an error is not likely to occur in the evaluation of sorption exothermicity based on temperature measurement. The dry air supply system needle valve 12 is not always needed, and the flow rate may be set at a certain flow rate.

The measuring method using the sorption exothermicity measurement device 1 according to the present embodiment 2 will be explained. The process of measuring temperature after the flowing of dry air or humidified air into the reaction measuring instrument 4 is the same as or similar to that in the embodiment 1 mentioned above. However, there is one difference from the embodiment 1 mentioned above in the process prior to the flowing of humidified air into the reaction measuring instrument 4. A detailed explanation will be given below.

The difference is in that the flow rate of humidified air is measured by the flow rate measuring instrument 5 and judgment whether the flow rate is a flow rate within a certain range or not and further subsequent judgments are performed by the controller 15. The detailed process is the same as or similar to that in the embodiment 1 mentioned above, and therefore, on the basis of the difference, the method for measuring sorption exothermicity according to the present embodiment 2 will be briefly commented with a flowchart form.

The controller 15 inputs the detected value of the flow rate from the flow rate measuring instrument 5 and regulates the humidified air supply system needle valve 13 so that the flow rate is a determined flow rate. Further, the detected value of temperature is input from the temperature sensor 7 and recorded at predetermined timing. Although not illustrated in FIG. 3, both of the air pump 2 and the switching valve 11 may also be controlled by the controller 15 to enable air to be supplied and the flow paths to be switched automatically.

In order to detect the flow rate, for example, a difference in pressure before and after a diaphragm, a difference in pressure before and after a plate, ultrasonic wave propagation time, or the like is measured using a diaphragm flowmeter (Venturi meter), a differential pressure flow meter, an ultrasonic flowmeter, or the like, and an electrical signal value indicating the flow rate is input. In order to regulate a flow rate, for example, an actuator is attached to an operator for a needle valve, and the movement of the actuator is controlled, whereby the flow rate can be regulated. In addition, flow rate measurement and flow rate regulation may be realized by any method.

Figure 4:
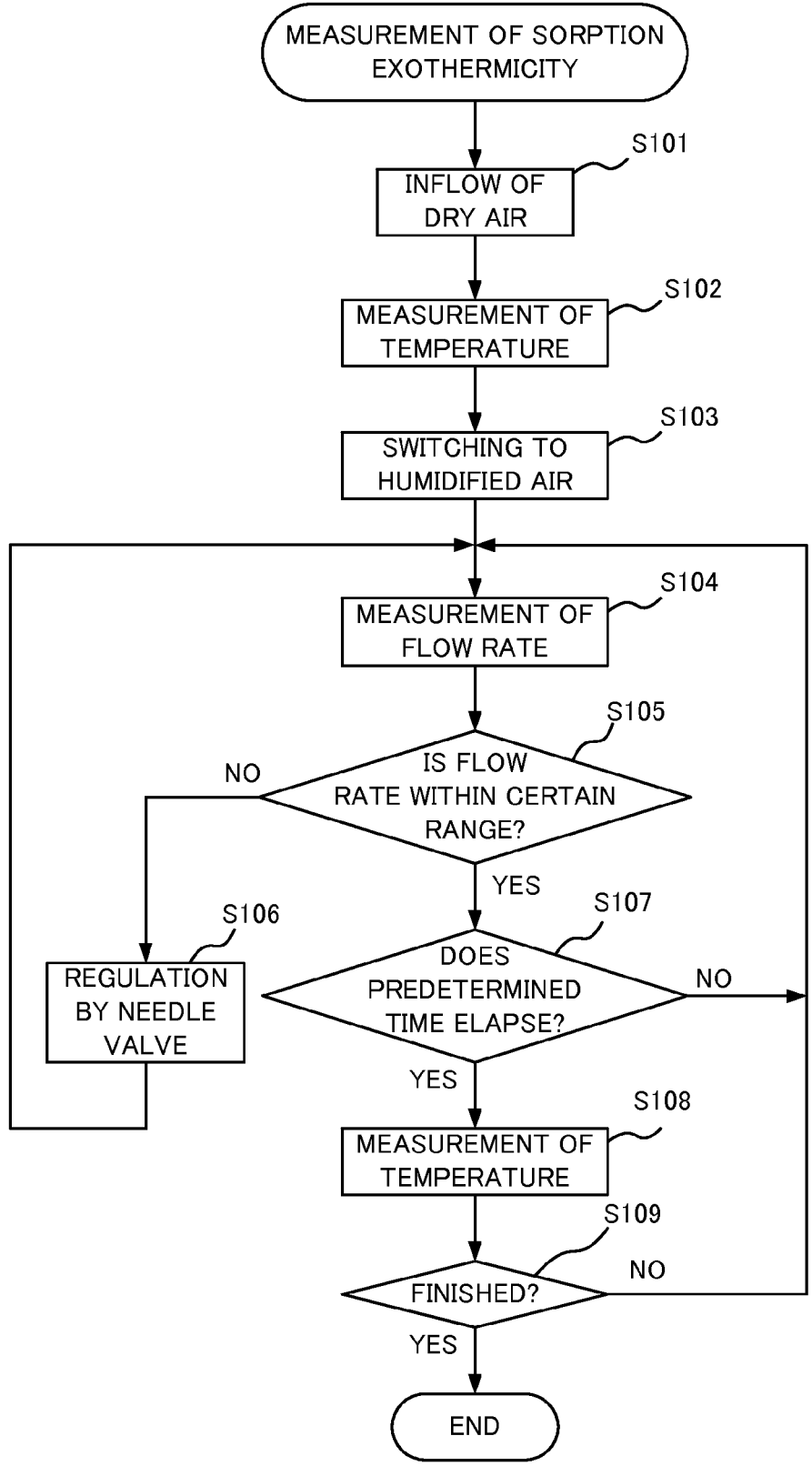
FIG. 4 is a flowchart showing an example of the operation of the measurement of sorption exothermicity according to Embodiment 2.

FIG. 4 is a flowchart showing an example of the operation of the measurement of sorption exothermicity according to Embodiment 2. First, as shown in FIG. 4, dry air is allowed to flow into the reaction measuring instrument 4 from a dry air supply system (step S101), and the temperature of the sample 10 is measured, for example, 1 to 2 minutes later (step S102). Then, the flow paths are switched by the switching valve 11 so that humidified air is supplied (step S103). In addition, the flow rate of humidified air is measured by the flow rate measuring instrument 5 (step S104). Here, it is judged whether the flow rate is within a certain range or not in the system of the controller 15 (step S105), and when the flow rate deviates from the certain range (step S105; NO), information is sent so that the regulation is automatically carried out in the humidified air supply system needle valve 13 (step S106). In such a manner, the flow rate of humidified air is appropriately regulated in the humidified air supply system needle valve 13, and a return to the stage of measuring the flow rate of humidified air is performed again (step S104).

When the flow rate is within the certain range (determined value) (step S105; YES), if predetermined time elapses (step S107; YES), the temperature of the sample 10 is measured (step S108). The predetermined time corresponds to, for example, a cycle for measuring temperature. The predetermined time can be appropriately determined according to a regulated flow rate, the material of the sample 10, ambient conditions, or the like. When the predetermined time does not elapse (step S107; NO), a return to the stage of measuring the flow rate of humidified air is performed again (step S104).

When the predetermined time elapses (step S107; YES), the temperature of the sample 10 is measured (step S108), and then, it is judged whether temperature measurement is finished or not (step S109). For example, when temperature measurement is performed plural times, if temperature measurement has not been finished a specified number of times (or for specified time) (step S109; NO), a return to the stage of measuring the flow rate of humidified air is performed again (step S104). When temperature measurement has been finished a specified number of times (or for a specified time) (step S109; YES), the measurement of sorption exothermicity is finished.

As described above, in the measuring method using the sorption exothermicity measurement device 1 according to the present embodiment 2, the flow rate of humidified air that directly flows into the reaction measuring instrument 4 is measured and regulated in the same or similar manner as in Embodiment 1, and therefore, the amount of given moisture per unit time can be controlled. As a result, the evaluation results of sorption exothermicity with more accuracy and improved reproducibility can be provided. Further, the method is simpler and more efficient since the controller 15 is also disposed.

(Embodiment 3)

Figure 5:
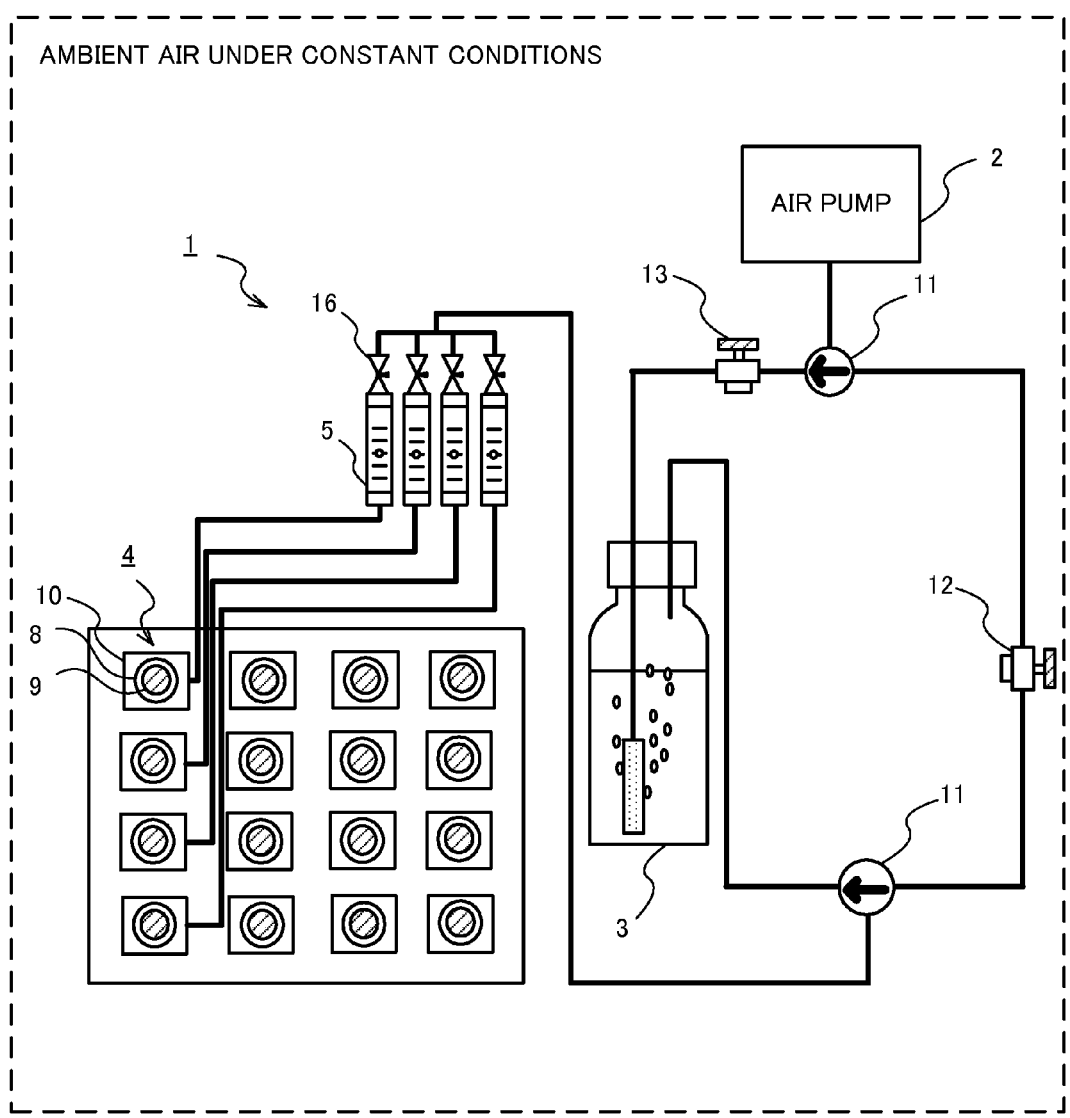
FIG. 5 is a schematic configuration diagram illustrating a sorption exothermicity measurement device according to Embodiment 3.

FIG. 5 is a schematic configuration diagram illustrating the sorption exothermicity measurement device 1 according to Embodiment 3. As illustrated in FIG. 5, the difference between the sorption exothermicity measurement device 1 according to the present embodiment 3 and the sorption exothermicity measurement device 1 according to Embodiment 1 mentioned above is in that, as a whole, a plurality of reaction measuring instruments 4 and a plurality of flow rate measuring instruments 5 are disposed and a needle valve 16 is disposed between each supply flow path and each flow rate measuring instrument 5.

A measuring method using the sorption exothermicity measurement device 1 according to the present embodiment 3 will be explained. The process of measuring temperature after flowing of dry air or humidified air into the plural reaction measuring instruments 4 is the same as or similar to that in Embodiments 1 and 2 mentioned above. Further, performance of the sorption exothermicity measurement in ambient air under constant conditions (for example, in a room with steady temperature and humidity, or the like) is the same as or similar to that in Embodiment 2 mentioned above. However, there is one difference from Embodiments 1 and 2 mentioned above. A detailed explanation will be given below.

In the method for measuring sorption exothermicity according to the present embodiment 3, the process before humidified air is supplied from the bubbling instrument 3 is the same as or similar to that in which Embodiments 1 and 2 mentioned above are combined. However, then, humidified air is divided into the plural flow paths, passes through the plural needle valves 16, and flow rates are measured by flow rate measuring instruments 5 connected to respective needle valves 16.

It is confirmed whether each measured flow rate is a flow rate within a certain range; and if the flow rate deviates from the certain range, the needle valve 16 connected to the flow rate measuring instrument 5 with the deviating flow rate is loosened or closed, for example, by manual operation to regulate the flow rate of humidified air to be a flow rate within the certain range. The humidified air regulated to have the flow rate within the certain range in each flow path flows into the reaction measuring instrument 4 connected to each needle valve 16 and each flow rate measuring instrument 5, and sorption exothermicity is evaluated by the same as or similar to measuring method in Embodiments 1 and 2 mentioned above. For the sample 10 measured in each reaction measuring instrument 4, various kinds of test pieces can be used.

In the case of the present embodiment 3, not only the dry air supply system needle valve 12 but also the humidified air supply system needle valve 13 is not always needed, and the flow rate may be set at a certain flow rate in advance. The humidified air supply system needle valve 13 may also be used for roughly regulating the amount of supplied humidified air. Although only the four flow paths are drawn in FIG. 5, the remaining flow paths of the reaction measuring instruments 4 are omitted, and an experiment on up to 16 kinds of test pieces can be simultaneously conducted in the actual sorption exothermicity measurement device 1 illustrated in FIG. 5.

As described above, in the measuring method using the sorption exothermicity measurement device 1 according to the present embodiment 3, the flow rate of humidified air that directly flows into each reaction measuring instrument 4 is measured and regulated in the same or similar manner as in Embodiment 1, and therefore, the amount of given moisture per unit time can be controlled. As a result, the evaluation results of sorption exothermicity with more accuracy and improved reproducibility can be provided. Further, the method is simpler and more efficient since sorption exothermicity can be evaluated for a large number of samples 10 in one operation.

(Embodiment 4)

Figure 6:
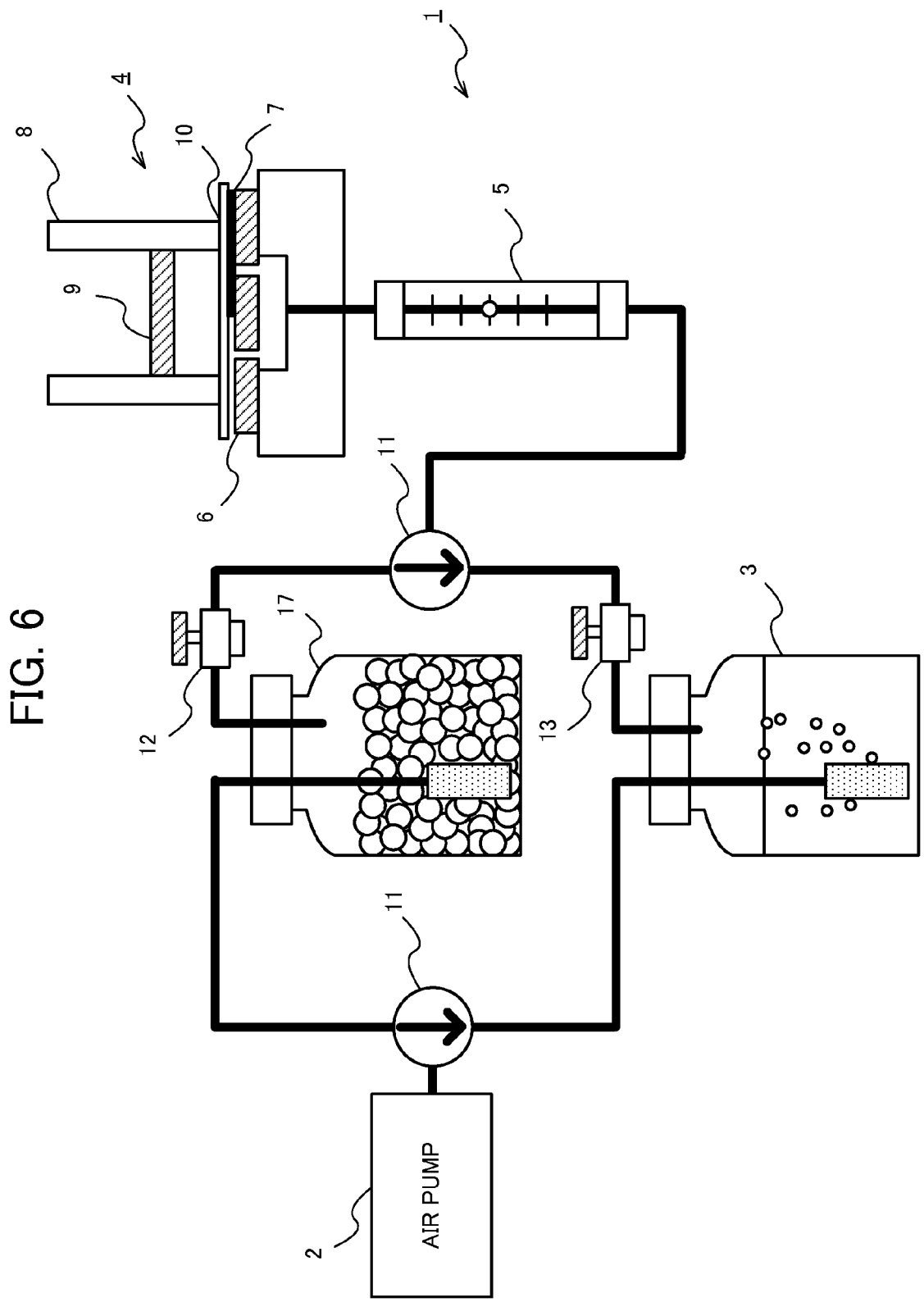
FIG. 6 is a schematic configuration diagram illustrating a sorption exothermicity measurement device according to Embodiment 4.

FIG. 6 is a schematic configuration diagram illustrating a sorption exothermicity measurement device according to Embodiment 4. As illustrated in FIG. 6, the difference between the sorption exothermicity measurement device 1 according to the present embodiment 4 and the sorption exothermicity measurement device 1 according to Embodiment 1 mentioned above is in that a silica gel filled tube 17 is disposed in the flow path that links the air pump 2 and the dry air supply system needle valve 12.

A measuring method using the sorption exothermicity measurement device 1 according to the present embodiment 4 is different only in that the dry air of the air pump 2 is passed through the silica gel filled tube 17 to allow more dried air to flow into the reaction measuring instrument 4, compared to the measuring method according to Embodiment 1 mentioned above. In other words, the difference between the measurement temperature of the sample 10 in dry air and the measurement temperature of the sample 10 in humidified air is increased. Any substance that absorbs moisture, such as calcium chloride, except silica gel, may be used.

As described above, in the measuring method using the sorption exothermicity measurement device 1 according to the present embodiment 4, the flow rates of dry air and humidified air that directly flow into the reaction measuring instrument 4 are measured and regulated, and therefore, the amount of given moisture per unit time can be controlled. As a result, the evaluation results of sorption exothermicity with more accuracy and improved reproducibility can be provided. Furthermore, since the measurement temperature difference between dry air and humidified air is increased, sorption exothermicity with a minute difference can be evaluated.

The present disclosure is not limited to the above-mentioned embodiments of the disclosure and the description of an example described below. Various modifications that can be easily achieved by those skilled in the art without departing from the subject matters in Claims are also within the scope of the disclosure. For example, embodiments in which the components of the embodiments 1 to 4 mentioned above are combined are within the scope of the disclosure.

Further, the regulation of the flow rate of air using the dry air supply system needle valve 12, the humidified air supply system needle valve 13, or the needle valve 16 may be replaced by fine adjustment using the air pump 2 or by regulation in combination of the instruments. Furthermore, a commercially available flowmeter with a valve, with which measurement and regulation of an air flow rate are simultaneously performed, may be connected. In addition, an instrument or a method for measuring and regulating an air flow rate, known to those skilled in the art, may be utilized.

The shape, configuration, and the like of the structural instruments of the sorption exothermicity measurement device or the reaction measuring instrument 4 illustrated in FIGS. 1 to 3, 5, and 6 are examples. Any shape, configuration, and the like are acceptable if the temperature of a test piece can be measured and sorption exothermicity can also be evaluated under the same conditions as in the present disclosure.

(Specific Example)

The preferred embodiment illustrated in above-mentioned FIG. 5 will be explained with a specific example.

The air supply system illustrated in FIG. 5 is configured using a commercially available instrument so that switching and supply of dry air (20° C.×40% RH) and humidified air (20° C.×90% RH) can be performed by the manual valve (switching valve 11). The dry air (20° C.×40% RH) is ambient air in a room with steady temperature and humidity. Commercially available flowmeters with valves are used as alternatives to each flow rate measuring instrument 5 and each needle valve 16.

The inside of a reaction measuring instrument 4 connected to each valve will be described. A first foam heat-insulating material 6 is a styrene foam plate having a thickness of 5 to 7 mm and measuring 50 mm per side, in which four discharge holes 14 ($\phi$ 5 mm) are formed on a circumference of a circle with a radius of 10 mm, and functions as simulated skin. A temperature sensor 7 is a film-like thin film temperature sensor and is fixed to the first foam heat-insulating material 6 with a double-faced tape. A sample holder 8 is a cylindrical plastic holder (40 mm in inner diameter/50 mm in outer diameter); and a position with a height of 2 mm from a position where a sample 10 is adhered is blocked with a styrene foam plate which is a second foam heat-insulating material 9 to form a residence air layer in measurement. Further, the sample 10 (measuring around 10 cm per side) is adhered to the bottom of the sample holder 8 with a double-faced tape without being wrinkled. In this case, the reverse side of the skin-contact side of the sample 10 which is a test piece of clothing is adhered to the sample holder 8. Then, the sample holder 8 is put on the face of the first foam heat-insulating material 6 to which the temperature sensor 7 is fixed (see FIGS. 1 and 2).

The present disclosure is not limited to the above-mentioned embodiments of the disclosure and the description of the specific example. Various modifications that can be easily achieved by those skilled in the art without departing from the subject matters in Claims are within the scope of the disclosure.

All of the contents of Unexamined Japanese Patent Application Kokai Publications shown in the present specification are incorporated herein by reference in their entirety.

The present application is based on Japanese Patent Application No. 2012-039260 filed on Feb. 24, 2012. Entire specification, claims, and drawings of Japanese Patent Application No. 2012-039260 are incorporated herein by reference.

REFERENCE SIGNS LIST

1 Sorption exothermicity measurement device
2 Air pump
3 Bubbling instrument
4 Reaction measuring instrument
5 Flow rate measuring instrument
6 First foam heat-insulating material
7 Temperature sensor
8 Sample holder
9 Second foam heat-insulating material
10 Sample
11 Switching valve
12 Dry air supply system needle valve
13 Humidified air supply system needle valve
14 Discharge hole
15 Controller
16 Needle valve
17 Silica gel filled tube

The invention claimed is:

1. A sorption exothermicity measurement device comprising:
a dry air supplier;
a humidified air supplier;
at least one reaction measurer into which dry air supplied from the dry air supplier or humidified air supplied from the humidified air supplier flows to allow the supplied dry air or the supplied humidified air to come in contact with a held sample;
a flow rate regulator that regulates a flow rate of at least the humidified air of the dry air or the humidified air flowing into the at least one reaction measurer; and
a flow rate measurer that measures the flow rate of at least the humidified air of the dry air or the humidified air flowing into the at least one reaction measurer wherein the at least one reaction measurer comprises:
a first layer that comprises a heat-insulating material, the first layer including therein a discharge hole through which inflow of the flowing dry air or humidified air occurs from one face and outflow of the dry air or the humidified air occurs toward the other face;
a temperature sensor that is placed on the face, toward which the outflow of the dry air or the humidified air occurs, of the first layer;
a sample holder that holds the sample sandwiched between the sample holder and the first layer such that temperature-sensing portion of the temperature sensor comes in contact with the sample in a periphery of a region containing the temperature sensor; and a second layer that comprises a heat-insulating material, the second layer being placed to face the first layer such that the sample is interposed between the first layer and the second layer in the region containing the temperature sensor.

2. The sorption exothermicity measurement device according to claim 1, wherein the at least one reaction measurer comprises a plurality of reaction measurers;

the flow rate regulator regulates the flow rate of the humidified air independently with respect to each of the plurality of reaction measurers; and the flow rate measurer measures the flow rate of the humidified air independently with respect to each of the plurality of reaction measurers.

3. The sorption exothermicity measurement device according to claim 2, further comprising a controller that regulates the flow rate regulator such that the flow rate measured in the flow rate measurer is a determined value.

4. The sorption exothermicity measurement device according to claim 1, further comprising a controller that regulates the flow rate regulator such that the flow rate measured in the flow rate measurer is a determined value.

5. A sorption exothermicity measurement method, comprising:

a drying step of allowing dry air to flow into a reaction measurer in which a sample is held;

a humidification step of allowing humidified air to flow into the reaction measurer in which the sample is held, after the drying step;

a measurement step of measuring a flow rate of the humidified air flowing into the reaction measurer in the humidification step;

a regulation step of regulating the flow rate of the humidified air flowing into the reaction measurer, measured in the measurement step, to a determined flow rate; and a temperature measurement step of measuring temperature by a temperature sensor placed near the sample held in the reaction measurer in a state in which the flow rate of the humidified air is regulated in the regulation step wherein:

the reaction measurer comprises a sample holder and a first layer that comprises a heat-insulating material, the first layer including a discharge hole through which inflow of the flowing dry air or humidified air occurs from one face and outflow of the dry air or humidified air occurs toward the other face; and in the temperature measurement step, the temperature is measured in a state in which the temperature sensor is placed on the other face, toward which the humidified air flows out, of the first layer and the sample holder holds the sample sandwiched between the sample holder and the first layer such that temperature-sensing portion of the temperature sensor comes in contact with the sample in a periphery of a region containing the temperature sensor.

6. The sorption exothermicity measurement method according to claim 5, wherein regulation to a flow rate in which a premeasured reference standard cloth has a specified temperature-rising characteristic is performed in the regulated step.

* * * * *